United States Patent
Li et al.

(10) Patent No.: US 6,499,338 B2
(45) Date of Patent: Dec. 31, 2002

(54) MOISTURE MANAGEMENT OF TEXTILES

(75) Inventors: Yi Li, Kowloon (HK); Weilin Xu, Kowloon (HK); Kwok-wing Yeung, Kowloon (HK); Yi-lin Kwok, Kowloon (HK)

(73) Assignee: Hong Kong Polytechnic University, Kowloon (HK)

( * ) Notice: Subject to any disclaimer, the term of this patent is extended or adjusted under 35 U.S.C. 154(b) by 0 days.

(21) Appl. No.: 09/811,829

(22) Filed: Mar. 20, 2001

(65) Prior Publication Data

US 2002/0043100 A1 Apr. 18, 2002

Related U.S. Application Data

(63) Continuation-in-part of application No. 09/553,287, filed on Apr. 20, 2000, now abandoned.

(51) Int. Cl.$^7$ ................................................. G01N 33/36
(52) U.S. Cl. ................................. 73/73; 73/38; 73/159; 73/29.01; 73/335.05; 73/335.06; 73/74; 324/694; 324/693; 19/66 R
(58) Field of Search ............................ 73/73, 37.7, 37, 73/38, 159, 29.01, 335.05, 335.06, 74; 324/694, 693; 19/66 R

(56) References Cited

U.S. PATENT DOCUMENTS

| 3,586,972 A | | 6/1971 | Tulleners |
| 3,638,478 A | | 2/1972 | Dietert et al. |
| 4,331,031 A | * | 5/1982 | Godrich et al. ................ 73/159 |
| 4,754,264 A | * | 6/1988 | Okada et al. ............. 340/573.5 |
| H000839 H | * | 11/1990 | Carlon ........................ 324/694 |

FOREIGN PATENT DOCUMENTS

| JP | 59-132350 | 7/1984 |
| SU | 2553885 | 3/1990 |

* cited by examiner

Primary Examiner—Hezron Williams
Assistant Examiner—Andrë K. Jackson
(74) Attorney, Agent, or Firm—Leydig, Voit & Mayer, Ltd.

(57) ABSTRACT

Moisture management indexes are determined for a textile sandwiched between two plates. Electrical conductors arranged in concentric opposing pairs are used to measure changes in electrical resistance of the fabric. A quantity of water (or other chosen liquid) is poured down a guide pipe and changes of resistance measured against time. From this data, specific indexes are determined, in a repeatable fashion, and used for determining moisture management characteristics of the fabric.

7 Claims, 7 Drawing Sheets

FIG. 10

| Fabric No. | $K_1$ | $K_2$ | H | $S_1$ | R | $\alpha_1 \times 10^{-3}$ | $\alpha_2 \times 10^{-3}$ | OMMC | Feature of the moisture management |
|---|---|---|---|---|---|---|---|---|---|
| 1 Polyester / cotton | 9.37 | 13.45 | 6.8 | 8735 | 0.639 | 16.4 | 10.7 | 7.14 | - Quick water absorption<br>- Quick drying<br>- Greatest differential liquid transport<br>- Best overall moisture management |
| 2 Polyester / Cotton | 2.05 | 1.29 | 8.3 | 6953 | 0.450 | 16.7 | 9.4 | 0.17 | - Slow water absorption<br>- Quick dry<br>- Good differential liquid transport<br>- The 2$^{nd}$ overall moisture management |
| 3 Cotton | 6.28 | 6.38 | 0.8 | 11827 | 0.002 | 1.65 | 1.67 | -0.77 | - Quick absorbency<br>- Slow dry<br>- Poor differential liquid transport<br>- Poor overall moisture management |
| 4 Polyester | 2.32 | 10.09 | 0 | 42019 | 0.035 | -2.94 | -1.17 | -0.64 | - low absorbency<br>- Slow dry<br>- Poor differential liquid transport<br>- Poor overall moisture management |
| Mean | 5.01 | 7.80 | 3.98 | 17384 | 0.282 | 7.95 | 5.15 | | |
| Standard Deviation | 3.02 | 4.51 | 3.63 | 14330 | 0.272 | 8.74 | 5.02 | | |

MOISTURE MANAGEMENT OF TEXTILES

This disclosure is a continuation-in-part of U.S. patent application Ser. No. 09/553,287 filed Apr. 20, 2000, now abandoned.

BACKGROUND OF THE INVENTION

1. Field of the Invention

The invention relates to moisture management of textiles.

2. Description of Prior Art

In the design of textile fabrics, or layers of fabrics as used in diapers, the manner in which moisture is absorbed, distributed and evaporated from the fabric is varied by changing the materials and/or the. structure. For various fabric applications in rainwear, sports equipment, medical dressings, incontinence pads and so forth, different properties, or combinations of properties or characteristics are required. Broadly stated, such applicable properties and characteristics are already known or empirically provided in practice. However, no satisfactory testing methods or equipment are available for scientifically measuring or testing fabrics, especially for complex fabrics.

SUMMARY OF THE INVENTION

It is an object of the invention to overcome or at least reduce this problem.

According to one aspect of the invention there is provided a method of determining moisture management indexes of a planar textile fabric piece by pouring a quantity of liquid onto an area of an upper surface of the piece, measuring changes in electrical resistance through the piece and within a plurality of laterally disposed electrically enclosed areas of upper and lower surfaces of the piece, and, based on the electrical resistances, computing indexes:

(i) $S_1$ and $S_2$, being accumulated liquid absorption of the upper surface of the piece and the lower surface of the piece, respectively; and (ii) H, being maximum difference of water content at the upper and lower surfaces.

The method may include computing an index R, the relative difference In accumulated water content between the upper and lower surfaces of the textile piece, being equal to a ratio $$R = \frac{S_2 - S_1}{S_1}$$

The method may include computing indexes $K_1$ and $K_2$, the initial liquid absorption speeds at the upper and lower surfaces, respectively.

The method may also include computing indexes α1 and α2, the drying rates at the upper and lower surfaces, respectively.

According to another aspect of the invention there is provided equipment for computing specific indexes relating to moisture management of a planar textile piece of fabric material comprising:

a pair of opposed plates having an array of corresponding exposed opposed electrodes displaced at intervals from one another to form pairs of electrodes between which a piece of fabric can be held, means connected to the electrodes for measuring changes in electrical resistance through the piece and developed laterally across electrically enclosed areas of upper and lower surfaces of the piece, means for recording those changes in electrical resistance with respect to time, and means for computing the indexes.

The electrodes are concentric electrical conductive rings displaced about a central region.

The equipment may include means for adjusting separation of the plates so as to apply different pressure to a fabric piece supported between the plates.

The electrodes may each be laid out rectangularly in plan over increasing surface areas about a central region.

BRIEF DESCRIPTION OF DRAWINGS

Equipment for and methods of determining moisture management indexes of a textile piece according to the invention will now be described by way of example with reference to the accompanying drawings in which:

FIG. 10 is a table of indices for fabrics No. 1 to 4; and

DETAILED DESCRIPTION OF PREFERRED EMBODIMENTS

Figure 1:
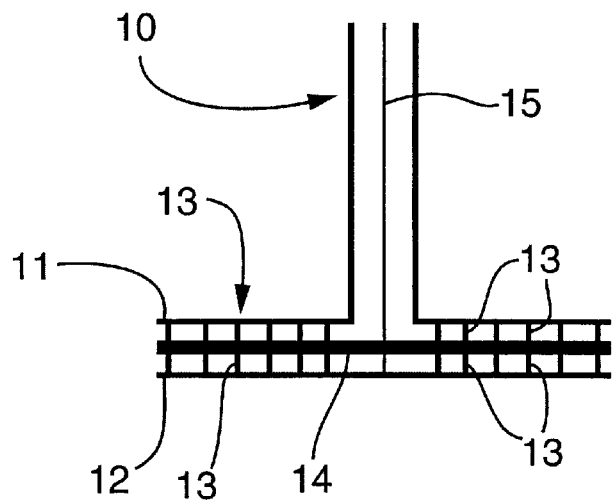
FIG. 1 is a schematic side view of a part of the equipment.
Figure 2:
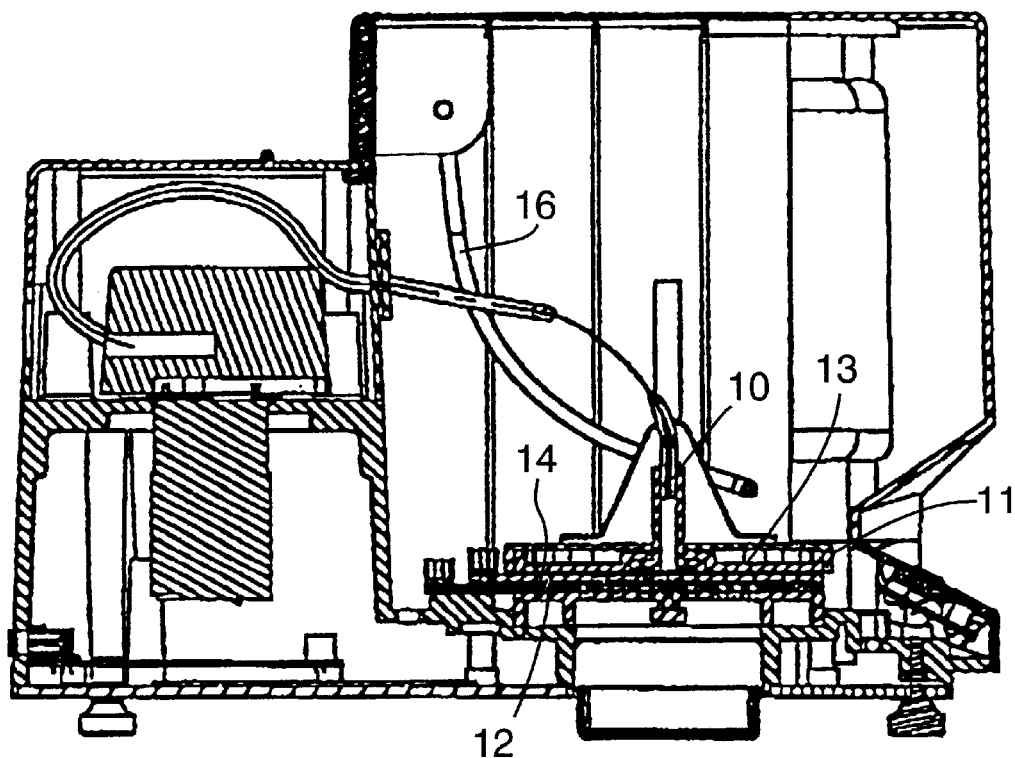
FIG. 2 is a sectional side view of the equipment.
Figure 3:
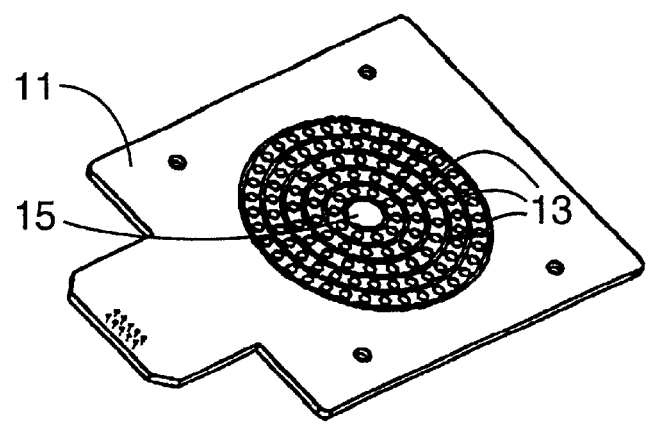
FIG. 3 is a plan view of one electrode plate of FIG. 1.

Referring to the drawings, in FIGS. 1 and 2, a water guide pipe 10 is provided above a pair of opposing plates 11 and 12, each plate including an array of concentric electrical conductors 13 as shown in FIG. 3. A textile fabric piece 14 is positioned between and held by the plates 11 and 12 for testing and in position by a central conductor pin 15. Electric wires, not shown, are connected to each opposing pair of conductors and voltages developed across the piece 14 at each pair are monitored as required. The voltages representing the effective resistance values of enclosed areas of upper and lower surfaces of the fabric are collected by a sensing module. The sensing module records the voltages, against time, for computing various indexes, as explained below.

In use, a quantity of water, or other liquid as appropriate, such as brine or urine solution, is poured into the guide pipe. The water flows onto a central region of an upper surface of the fabric piece and is absorbed by the fabric piece. Voltage measurements are recorded so that indexes, which correspond to the quantity and the rate that the water passes through and laterally along the fabric piece from the central region, can be computed.

These voltages, V, are measured according to a schematic circuit shown in FIG. 10 (where $R_{1mr}$ is a fixed 1 megaohm resistor).

Thus, $$V_i = V_i = \frac{V_o \cdot R_f}{1000 + R_f}$$

where $R_f$ is the resistance of the fabric, using an 1000 ohm fixed resistor.

$R_f$ is a known function of moisture content so that moisture content can be expressed as:
$M_i$=constant $$M_i = \frac{V_c - V_i}{V_i}$$

where $V_o$ equals the battery (i.e. applied) voltage, and $V_1$ equals the voltage between the innermost pair of conductors. The total of the water content U can be computed at each surface according to $$U = \sum_{i=1}^{6} M_i$$

(if there are six pairs of conductors)

Figure 4:
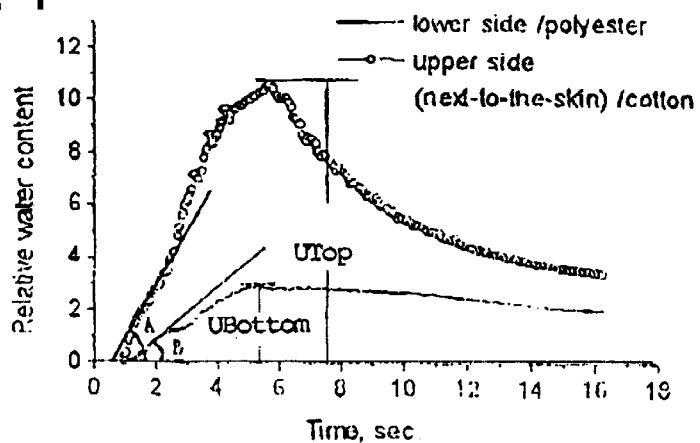
FIG. 4 is a graph of water content and time.

In FIG. 4, the graph shows a typical graph of U against time in seconds for the upper (upside) and lower (bottom side) surfaces of the fabric. An initial slope of each curve represents initial water absorption rates (K) at the two surfaces, so that $K_1$=tan A, and $K_2$=tan B.

The maximum difference of water content at the two surfaces H is given according to the expression:

$$H = U_{TOP}(max) - U_{bottom}(max)$$

Figure 5:
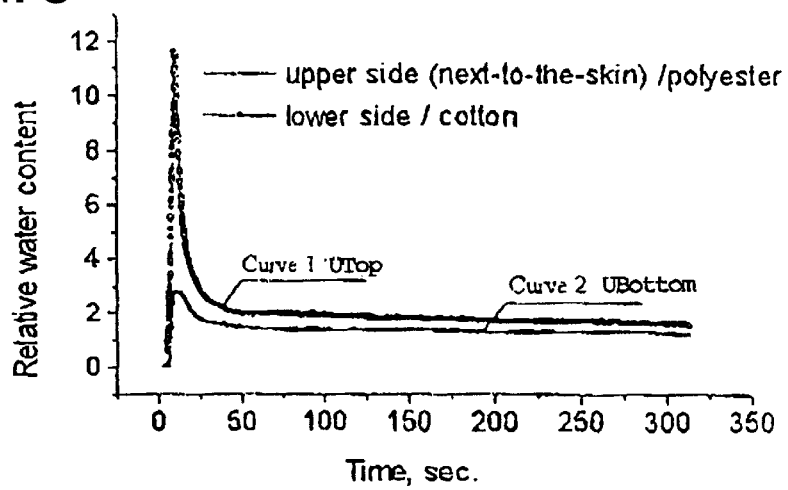
FIG. 5 is an another graph of water content and time.
Figure 6:
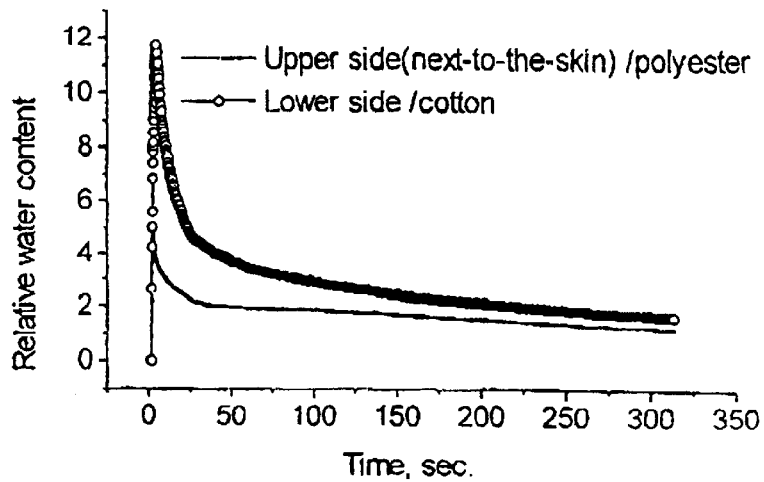
FIG. 6 is a graph of relative water content against time for polyester covered cotton fabric, fabric No. 1.
Figure 7:
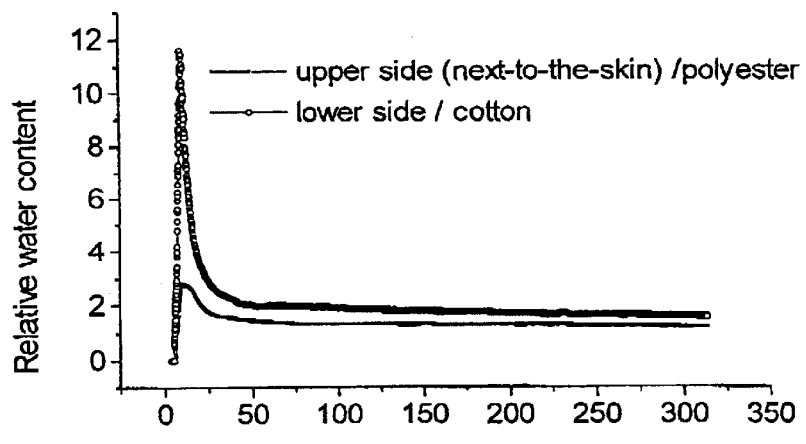
FIG. 7 is a graph of relative water content against time for polyester covered cotton fabric, fabric No. 2.
Figure 8:
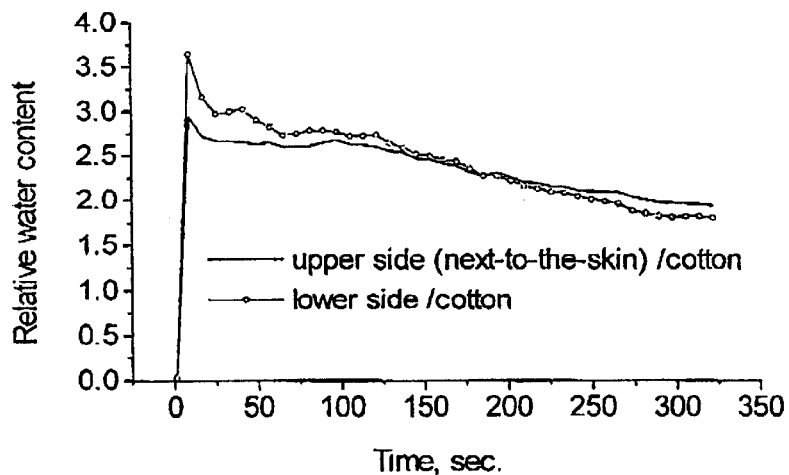
FIG. 8 is a graph of 100% cotton knitted fabric, fabric No. 3.
Figure 9:
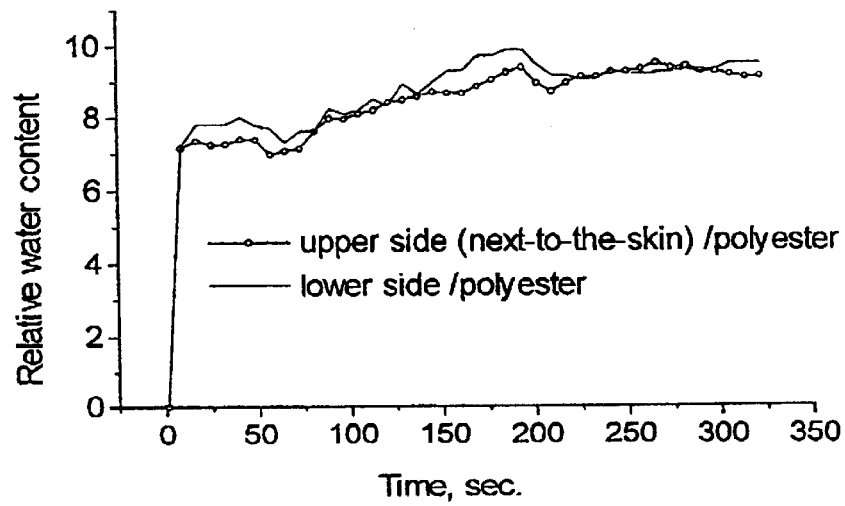
FIG. 9 is a graph of 100% polyester knitted fabric, fabric No. 4.
Figure 11:
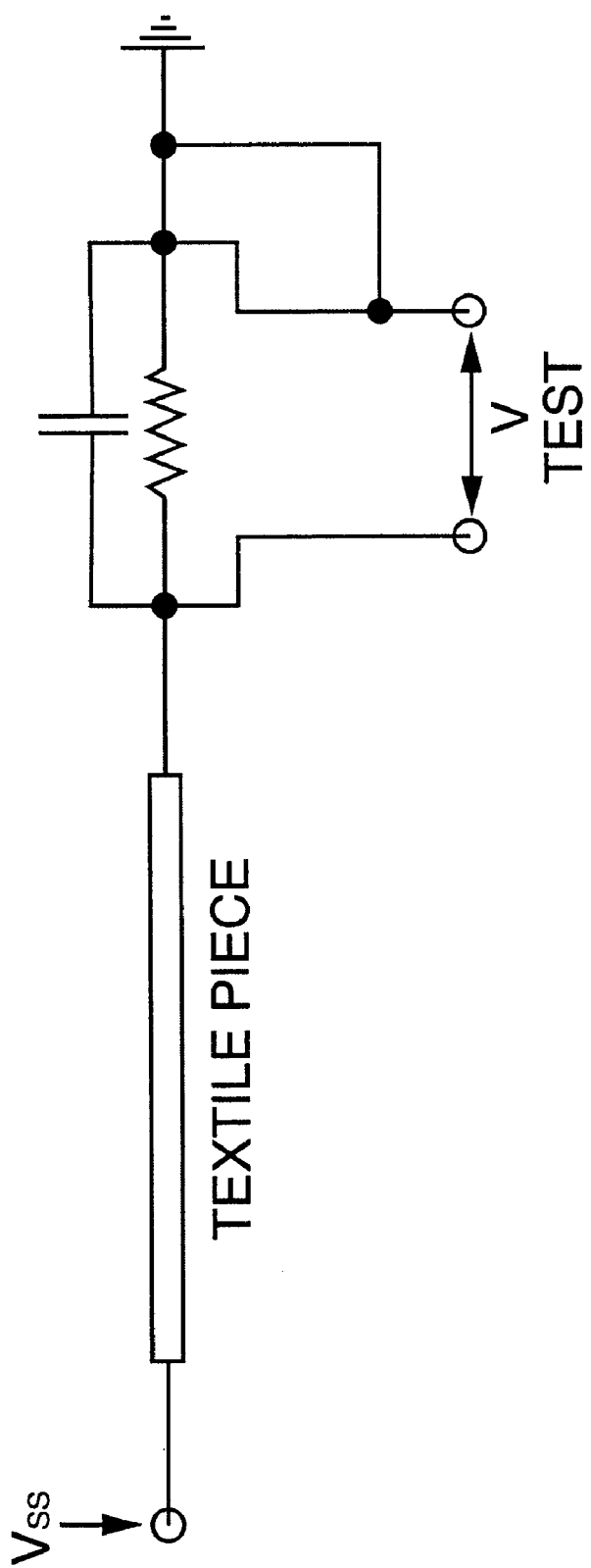
FIG. 11 is a schematic circuit for the equipment.

The graph in FIG. 5 is used to compute the accumulated content (S) and the relative difference (R) in accumulated water content between the upper and lower surface of the textile piece.

Thus $S_1 = \int U_{Top} dt$ and $S_2 = \int U_{bottom} dt$ and $$R = \frac{S_2 - S_1}{S_1}$$

FIGS. 6 to 9 are graphs of U plotted against time for different material fabric pieces.

For each pouring of a quantity of water, the moisture content will increase to a maximum value, and then the moisture content starts to decrease expotentially due to evaporation. The water content (U) decreases according to $$U = A \exp(-\alpha.t)$$

It will be appreciated that α can be derived for both surfaces.

Overall moisture management capacity of a fabric, which indicates the fabric's capability of quick liquid absorbency, one-way moisture transport and quick dry, is defined as:

$$OMMC = 0.25 \times \frac{K_2 - \overline{K}_2}{\sigma_{k2}} + 0.5 \times \frac{R - \overline{R}}{\sigma_R} + 0.25 \times \frac{\alpha_2 - \overline{\alpha}}{\sigma_{\alpha 2}}$$

The larger the OMMC is, the higher the overall moisture management capability of the fabric is.

Thus, the described equipment and the methods provide meaningful indexes that are based on measurements of voltages against time when a textile fabric piece is tested using a quantity of suitable liquid. Although resistance measurements have been used in the past for determining fabric characteristics, they have not made use of transverse migration of liquid in the fabric or provided useful repeatable indexes relating to moisture management. Known tests include dropping water onto a textile piece surface and visually observing its migration. Such observations are unreliable, especially if the fabric is dark-coloured, or in situations when the water spreads very quickly. By contrast, embodiments of this invention can provide accurate, repeatable and meaningful test information for each single fabric piece, or for multi-layered fabric pieces, if required.

In addition, the plates 11 and 12 may be arranged to be relatively movable or adjustable in a manner to apply different pressures between the electrodes against the fabric pieces, or layers of fabric pieces, during testing. Clearly it is important for some applications or uses to determine what chances in the moisture management of the textile pieces will occur due to applied pressure. Such information is useful for fabric materials that will be subjected to changes, in such pressure, during use.

The Table in FIG. 10 shows the results of testing four different fabrics. It can be readily deduced from the Table that all four fabrics have a relatively good moisture absorption rate, although fabric No. 1 is the best. In terms of one-way transport of water, Fabric No. 2 appears to be better than the other fabrics initially. Over a longer period however, Fabric No. 1 is better than Fabric No. 2, Fabric No. 3 and Fabric No. 4 show in effect no one-way transport capability. In terms of drying speed, Fabric No. 1 and Fabric No. 2 are similar, showing good quick-dry behaviour. Meanwhile, Fabric No. 3 shows poor drying behaviour and Fabric No. 4 shows no sign of drying within the test period. In term of overall moisture management as shown by OMMC values, Fabric No. 1 has the best performance, followed by Fabric No. 2. Fabric No. 3 and Fabric No. 4 show unsatisfactory performances.

Thus it can be immediately deduced that, for example, Fabric No. 3 and No. 4 would be unsuitable for sports clothing generally, although such fabrics may be suitable and advantageously used for inner liners of outdoor athletic clothing. It can also be deduced that, for example, Fabrics No. 3 and No. 4 would be unsuitable for sportswear and incontinence products for use next-to-the skin, as such Fabrics will not keep the skin dry and comfortable when liquid is discharged from the body. Fabric No. 2 will perform better than Fabric No. 3 and No. 4 for sportswear and incontinence products, as Fabric No. 2 has relatively good differential transport capability and will quickly dry. Fabric No. 1 will be the best for sportswear and a next-to-skin layer of incontinence products, as it has the best moisture management capability and individual aspects of performance in terms of differential liquid transport, water absorbing, and drying rates.

Figure 12:
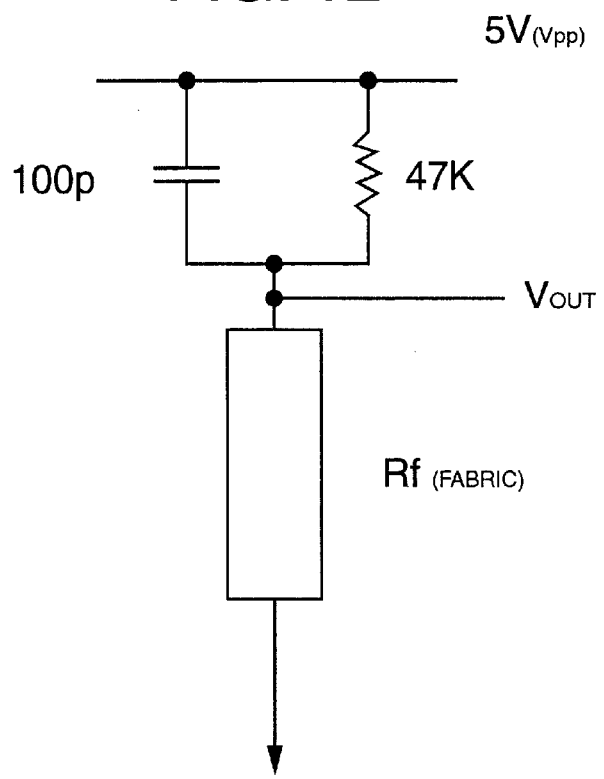
FIG. 12 is an alternative schematic circuit for the equipment.

In another preferred embodiment for computing moisture management indexes, the fixed resistor in FIG. 12 is chosen to be 47 kΩ ($R_{ref}$), thus, if $R_f$ is the resistance of the fabric:

$$V_{OUT} = V_{DD} \times \frac{R_f}{47k + R_f}.$$

$R_f$ is a known function of moisture content so that moisture function (M) can be expressed as:

$$Mi = \frac{1}{Ai \cdot R_f} = \frac{V_{DD} - V_{OUT}}{Ai \cdot 47k \cdot V_{OUT}}$$

where $V_{DD}$ equals the battery (i.e. applied) voltage, and $V_{OUT}$ equals the voltage between a pair of conductors. The total of the water content at each surface can be computed (if there are six pairs of conductors) as:

$$U_{TOP} = \sum_{i=1}^{6} M_{TOPi} \text{ and } U_{Bottom} = \sum_{i=1}^{6} M_{Bottomi}$$

Maximum Absorption Rate

In FIG. 4, the graph shows a typical graph of U against time in seconds for the upper (upside) and lower (bottom side) surfaces of the fabric. The maximum slope of each curve represents the maximum water absorption rates (S) at the two surfaces, so that $S_{TOP}$=Maximum [slope($U_{TOP}$)], and $S_{Bottom}$=Maximum [slope($U_{bottom}$)]

One Way Transport Capability

The graph in FIG. 5 is used to compute the one way transport capability (R) on the basis of the difference in accumulated water content between the upper and lower surface of the textile piece:

$R$=[Area($U_{bottom}$)−Area($U_{TOP}$)]/Total Testing Time

The graphs of U plotted against time in FIGS. 6 to 9 for different material fabric pieces are used as before.

Wetting Time

Wetting time ($W_t$ and $W_b$) is defined as time when the slope of total water content ($U_{TOP}$ or $U_{bottom}$) become greater than Tan (15°) for the top and bottom surfaces respectively.

Maximum Wetted Radius (WR)

Maximum wetted radius ($WR_{top}$ and $WR_{bottom}$) is defined as maximum wetted ring radius at the top and bottom surfaces, where the slope of total water content ($M_{topi}$ or $M_{bottomi}$) become greater than Tan (15°) for the top and bottom surfaces respectively.

Spreading Speed (mm/sec)

Spreading speed ($SS_{top}$ and $SS_{bottom}$) is defined as $SS=WR/t_{wr}$, where $t_{wr}$ is the time to reach the maximum wetted ring for the top and bottom surfaces respectively.

This other preferred arrangement is more useful in an industrial application. The set of 9 indexes and equations are able to provide more convenient and more meaningful results for practical usage. Wetting time (W) can be compared with a traditional drop test. The equations for calculating maximum absorption rate (S) and one way transport capability (R) are more conveniently applicable to software replication. Maximum wetted radius (WR) and spreading speed (SS) provide additional information on the geometric distribution of liquid moisture in the fabrics.

Figure 13:
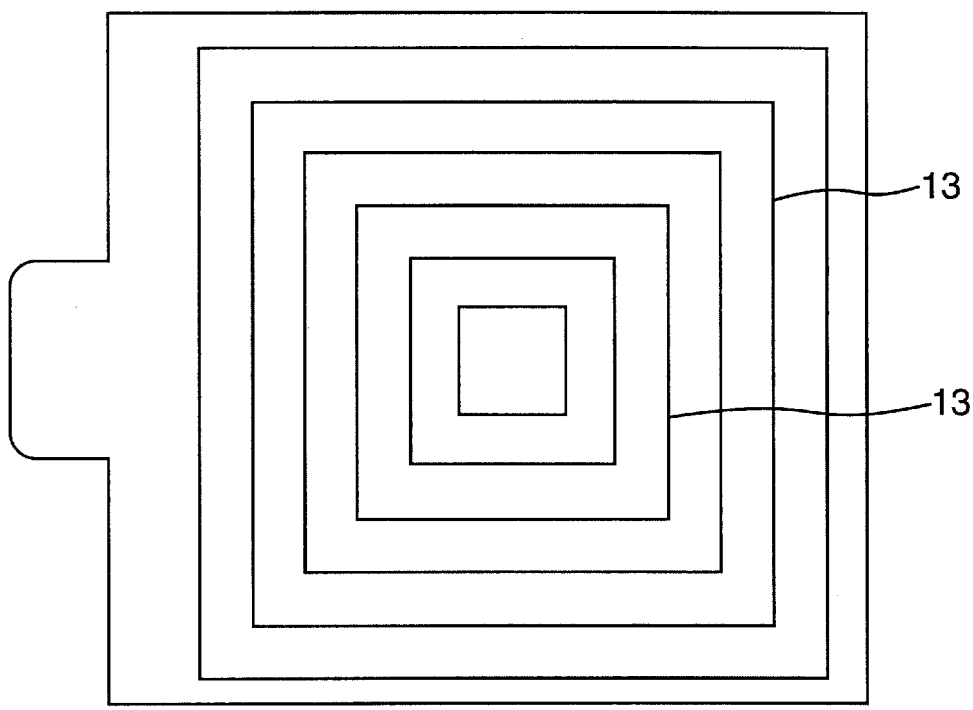
FIG. 13 is a diagrammatic plan view of another electronic plate of FIG. 1.
Figure 14:
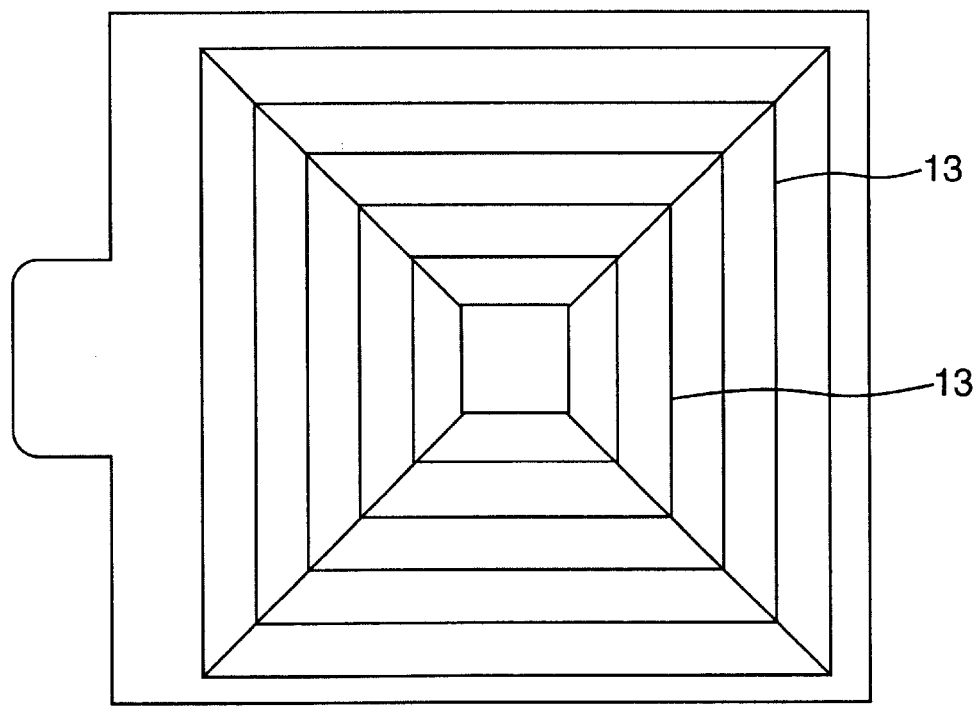
FIG. 14 is a diagrammatic plan view of a further electrode plate of FIG. 1.

FIGS. 13 and 14 show other suitable configurations for the electrodes 13. The configurations enable the changes of effective resistance to be sensed, by measuring voltages, in the same manner as before, within a plurality of enclosed areas of the upper and lower surfaces of the fabric. The electrodes in FIG. 13 are each laid out rectangularly in plan and, in FIG. 14 extra 'diagonal' electrodes are provided to enable the effective resistance of extra or different electrically enclosed surface areas to be measured.

What is claimed is:

1. A method of determining moisture management indexes of a piece of a planar textile fabric including pouring a quantity of liquid onto an area of a first surface of a planar textile fabric piece, measuring changes in electrical resistance through the fabric and within a plurality of laterally disposed electrically enclosed areas of the first surface and a second surface of the fabric, opposed to the first surface, and, based on the electrical resistances, computing indexes:

(i) $S_1$ and $S_2$, accumulated water content of the first surface of the fabric and the second surface of the fabric, respectively; and (ii) H, maximum difference of water content at the first and second surfaces.

2. The method according to claim 1, including computing an index R as ability of the fabric to transport liquid across a thickness as a ratio $$R = \frac{S_2 - S_1}{S_1}.$$

3. The method according to claim 1, including computing indexes $K_1$ and $K_2$ as initial liquid absorption speeds at the first and second surfaces, respectively.

4. The method according to claim 1, including computing indexes α1 and α2 as drying rates at the first and second surfaces, respectively.

5. An apparatus for computing specific indexes relating to moisture management of a planar textile piece of fabric material, the apparatus comprising:

a pair of opposed plates, each plate having an array of exposed opposed electrodes displaced at intervals from one another, the plates providing pairs of electrodes between which a piece of fabric, having opposed first and second surfaces, can be held, means connected to the electrodes for measuring changes in electrical resistance through the fabric when liquid is added onto the first surface of the fabric, wherein the electrical resistance is developed laterally across electrically enclosed areas of the first and second surfaces of the fabric, means for recording the changes in electrical resistance with respect to time, and means for calculating the accumulated water content of the first surface of the fabric and the second surface of the fabric from the changes in electrical resistance with respect to time.

6. The apparatus according to claim 5, in which the electrodes are concentric electrically conductive rings displaced about a central region.

7. The apparatus according to claim 5, in which the electrodes are each laid out rectangularly in plan over increasing surface areas about a central region.

* * * * *